US006835858B1

(12) United States Patent
De Jonge et al.

(10) Patent No.: US 6,835,858 B1
(45) Date of Patent: Dec. 28, 2004

(54) CATALYTIC CONVERSION OF AN ORGANIC CARBONATE

(75) Inventors: Johannes Petrus De Jonge, Amsterdam (NL); Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/659,142

(22) Filed: Sep. 10, 2003

(30) Foreign Application Priority Data

Sep. 12, 2002 (EP) .............................. 02256347

(51) Int. Cl.$^7$ ................................ C07C 39/00
(52) U.S. Cl. ................. 568/716; 558/274; 558/277; 568/858; 568/888; 568/889; 568/890
(58) Field of Search ................ 568/716, 858, 568/888, 889, 890; 558/274, 277

(56) References Cited

U.S. PATENT DOCUMENTS

| | | | | | |
|---|---|---|---|---|---|
| 5,218,135 | A | * | 6/1993 | Buysch et al. | 558/277 |
| 5,489,702 | A | * | 2/1996 | Doya et al. | 558/277 |
| 2003/0078448 | A1 | * | 4/2003 | Buchanan et al. | 558/277 |

FOREIGN PATENT DOCUMENTS

| JP | 2188541 | 7/1990 |
|---|---|---|
| JP | 6239806 | 8/1994 |

* cited by examiner

*Primary Examiner*—Michael L. Shippen

(57) ABSTRACT

The invention relates to a method for the catalytic conversion of organic carbonate to the corresponding alcohol, wherein the organic carbonate is contacted with alcohol and/or water in the presence of a zinc supported catalyst.

10 Claims, No Drawings

CATALYTIC CONVERSION OF AN ORGANIC CARBONATE

FIELD OF THE INVENTION

The present invention relates to a method for the catalytic conversion of an organic carbonate using a zinc supported catalyst.

BACKGROUND OF THE INVENTION

JP-A-02188541 relates to converting propylene carbonate with water in the presence of a Lewis acid such as zinc chloride and a nitrogen containing organic base.

JP-A-6239806 relates to a method for the catalytic transesterification of alkylene carbonate with alcohol in the presence of a zinc oxide catalyst in particulate form.

It would be useful to provide a method for the catalytic conversion of organic carbonate, having an improved conversion rate and improved yield.

SUMMARY OF THE INVENTION

The present invention provides a method for the catalytic conversion of an organic carbonate to the corresponding diol, wherein the organic carbonate is contacted with alcohol and/or water in the presence of a zinc supported catalyst.

DETAILED DESCRIPTION OF THE INVENTION

The invention is based on the insight that by the use of a catalyst having zinc in supported form, the conversion rate and yield are improved. This zinc supported catalyst may be used in an alcoholysis (reaction with alcohol) or hydrolysis (reaction with water) or in a combined hydrolysis and alcoholysis.

The zinc supported catalyst is a catalyst in which the reactive zinc particles (presumably in the form of zinc oxide particles during the reaction) are kept apart by the support. The support may therefore consist of a material onto which zinc particles are deposited. It may also consist of an additive that is incorporated between the zinc particles. Preferably, the zinc of the present catalyst is in the form of zinc oxide and/or zinc hydroxide.

The zinc supported catalyst may be represented by the formula $Zn/M_xA_y$, wherein M is a metal (such as chromium, copper) and A is a non-metal (such as carbon, oxygen, sulfur, or a halide) and x and y may be independently 0–3. The support may comprise a material which is substantially inert in the catalytic conversion reaction or may be active in the catalytic conversion reaction. Examples of substantially inert support materials are silicon dioxide, titanium dioxide, zirconium dioxide, chromium (III) oxide ($Cr_2O_3$) and carbon. Examples of reactive support materials are aluminum oxide ($Al_2O_3$) and magnesium oxide (MgO). The zinc may also be supported in the form of a (metal) grid with other reactive and/or inert grid materials. Furthermore, the zinc supported catalyst according to the invention may comprise further inert or active additives, such as copper and copper oxide (CuO).

If the zinc supported catalyst comprises a support material, it is preferred to produce the zinc supported catalyst by impregnation with a zinc salt from solution or from a melt. Such impregnation process will result in a zinc supported catalyst having a high catalytic activity. However, other methodologies can be adopted for depositing zinc onto a support. These include, for example, the precipitation of zinc salt or the gas- or liquid-phase deposition of metallic or organometallic zinc species. When the impregnation is carried out using a zinc salt solution, this results in a zinc supported catalyst having a better catalyst performance.

A supported zinc catalyst can also be prepared by inserting components between zinc particles, e.g. via co-precipitation or co-kneading of a zinc salt with the salt of an other metal such as chromium.

In order to obtain a zinc supported catalyst having a long-term stability and a low leaching rate (loss of metal per kg of liquid product produced), it is preferred to subject the zinc supported catalyst to calcination at temperatures of 200–800° C., preferably of 300–700° C., more preferably of 400–600° C.

The carbonates suitable for use in the catalytic conversion method according to the invention may be ($C_1$–$C_8$) dialkyl carbonates, wherein the alkyl groups (straight, branched and/or cyclic) may be the same or different, such as methyl, ethyl, propyl and cyclohexyl; ($C_5$–$C_9$) diaryl carbonates, wherein the aryl groups may be the same or different, such as phenyl; and ($C_1$–$C_8$) alkyl ($C_5$–$C_9$) aryl carbonates or ($C_5$–$C_9$) aryl ($C_1$–$C_8$) alkyl carbonates, wherein the alkyl and the aryl group are defined above; and mixtures thereof. The alkyl and/or aryl groups can be linked together to form a cyclic carbonate such as the 1,2-carbonates (alkylene carbonate) of ethylene, propylene, butadiene, cyclohexene and styrene, the 1,3-carbonates of 1,3-propene diol and 1,3-butane diol, the 1,4-carbonate of 1,4-butane diol. Preferred as alkylene carbonates are ethylene carbonate and propylene carbonate.

It is noted that the alkyl group may be substituted with a ($C_5$–$C_9$) aryl group (aryl alkyl group) or ($C_2$–$C_{10}$) alkylene group (alkylene alkyl group). The aryl group may be substituted with an ($C_1$–$C_8$) alkyl group (alkylaryl group) or ($C_2$–$C_{10}$) alkylene group (alkylene aryl group). The alkylene group may be substituted with an ($C_1$–$C_8$) alkyl group (alkyl alkylene group) or ($C_5$–$C_9$) aryl group (aryl alkylene group). The substituents may be exemplified as mentioned above.

The alcohol may be an aromatic and/or aliphatic alcohol. The alcohol may be monohydric or polyhydric. The aliphatic alcohol comprises at least one ($C_1$–$C_{30}$) alkyl group which may be straight, branched and/or cyclic. The aliphatic alcohol may be saturated or unsaturated wherein the aliphatic alcohol is saturated or unsaturated. Preferred are ($C_1$–$C_{10}$)-alkylalcohol, more preferably ($C_1C_5$)alkyl alcohol or combinations thereof. Preferred are methanol and ethanol. Examples of polyhydric alcohols are diols such as glycol.

An example of an aromatic $C_5$–$C_9$ alcohol is phenol.

The support material may have a pre-shaped form. This form may be globular, circular, cylindrical and/or any desired or arbitrary molded, pressed or extruded form, including monolithic form or even a powder with an average particle size suitable for carrying out the reaction, such as larger than about 100 mm.

If the method according to the invention comprises a catalytic conversion by combined hydrolysis and alcoholysis then generally the molar ratio between water and alcohol lies between 1:1 and 1:100, preferably between 1:5 and 1:20.

Although the method for the catalytic conversion is suitable for any dialkyl carbonate conversion, it is preferred to use as a dialkyl carbonate an alkylene carbonate such as ethylene carbonate and propylene carbonate. Ethylene and propylene carbonate are most preferred. In the alcoholysis, the use of methanol is preferred. The combined hydrolysis and alcoholysis in the catalytic conversion according to the method of the invention results in a flexibility in the production of the corresponding diols and dialkyl carbonate together (alcoholysis) or to a production directed to the diol predominantly or solely with the simultaneous formation and release of carbon dioxide.

The reactor temperature was then raised to 160° C. for 16 hours to simulate an enhanced deactivation and metal leaching.

Results on methanolysis

TABLE 1

Performance of zinc supported catalysts and reference catalysts in the methanolysis of PC (120° C., 25 bara, WHSV = 5 gr/gr/h with MeOH:PC molar ratio of 4:1)

| Catalyst | $T_{calc}$ ° C. | Convers. MeOH [a] | PC [b] | Yield DMC [a] | MPG [b] | light ends [b] | MPC [b] | DMC:MPG [c] | Leaching [d] |
|---|---|---|---|---|---|---|---|---|---|
| $Zn.Cr_2O_3$ | — | 12.0 | 16.9 | 7.2 | 15.2 | 0.1 | 1.7 | 0.95 | 0.5 |
| $CuZn.Al_2O_3$ | — | 11.4 | 16.5 | 7.6 | 14.6 | 0.2 | 0.0 | 1.04 | — |
| 10% $Zn/SiO_2$ | 120 | 18.6 | 28.3 | 12.4 | 26.9 | 0.2 | 0.0 | 0.93 | — |
| 10% $Zn/SiO_2$ | 120 | 20.3 | 31.8 | 12.1 | 28.8 | 0.1 | 3.0 | 0.84 | 2.7 |
| 10% $Zn/SiO_2$ | 450 | 9.8 | 14.1 | 4.8 | 10.3 | 0.0 | 3.8 | 0.93 | 0.15 |
| 10% $Zn/Al_2O_3$ | 120 | 5.1 | 7.5 | 1.8 | 3.7 | 0.0 | 3.7 | 0.95 | 1.8 |
| 10% $Zn/Al_2O_3$ | 450 | 6.6 | 8.9 | 3.0 | 6.0 | 0.0 | 2.8 | 1.00 | 0.1 |

[a] expressed in mole % based on methanol;
[b] expressed in mole % based on PC;
[c] expressed in mole:mole;
[d] mg of metal per kg of liquid product
PC = propylene carbonate;
DMC = dimethylene carbonate;
MPG = monopropylene glycol;
MPC = methyl-propanolyl-carbonate.

The method and use of the catalyst according to the invention will be further elucidated by reference to the following examples, which are provided for illustrative purposes and to which the invention is not considered to be limited.

EXAMPLE 1

Catalyst preparation

The $Zn/M_xO_y$ catalysts were prepared by incipient wetness impregnation of $SiO_2$ (56 m$_2$/g), $Al_2O_3$ (287 m$^2$/g) or Al-stabilized MgO (53 m$^2$/g) with an aqueous zinc nitrate solution up to a zinc loading of 10 w %. The particles were then dried at 120° C., calcined for 2 hours at a temperature of 450° C. and crushed to a fraction of 30–80 mesh.

$Zn.Cr_2O_3$ (Engelhard Zn-0312-T1/4) and $CuZn.Al_2O_3$ (Katalco 83-3M) catalysts were commercial catalysts, which were presumably prepared by the conventional co-kneading and co-precipitation method (see e.g. A. B. Stiles in 'Catalyst Manufacture: laboratory and commercial preparations' Dekker Inc. (1983)).

Catalytic testing was performed in a so-called 6 tubular nanoflow unit. This unit has 6 quartz reactors with an internal diameter of 3 mm. Each reactor was loaded with 0.15 gram of catalyst (0.2–0.6 mm diameter) that was diluted in 0.45 gram of SiC (0.05 mm diameter). 0.45 g of SiC were placed on top of this bed and used as feed pre-heater.

Once loaded, the catalysts were dried in situ under $N_2$-flow at 120° C. and atmospheric pressure for 1 hour. The reactors were then pressurized to 25 bar and a 4:1 molar mixture of methanol and propene carbonate was fed to the reactor at a flow rate of 5 gr/(gr cat*hr), together with a $N_2$ flow of 1.7 nL/(gr cat*hr).

After an initial period of 20 hours at 120° C., the reactors were operated for 24 h, during which the liquid products were continuously condensed for off-line product analysis.

The examples reported in Table 1 clearly show the catalytic activity of catalysts prepared by impregnation of $SiO_2$, $Al_2O_3$ or Al-stabilised MgO with a zinc nitrate solution. These catalysts perform better than catalysts prepared by impregnating $SiO_2$ with a Mg-nitrate solution, which provided DMC and MPG at yields of 1.2 and 1.5 mole %, respectively, under similar conditions.

Even better catalytic performances are achieved with zinc based materials that combine a high surface area and a high zinc content. This is the case for the $Zn.Cr_2O_3$ (59 w % Zn and 130 m$^2$/g) and $CuZn.Al_2O_3$ catalysts (22 w % Zn and 56 m$^2$/g). These high-surface-area zinc rich materials exhibit a catalytic activity that is comparable to that of an Al-stabilised MgO.

Furthermore, Table 1 shows that a calcination of the zinc based catalyst precursors to high temperature, e.g. 400–600° C., is favorable for their long-term stability. It reduces the leaching rate of zinc components.

Results on hydrolysis

A PC-hydrolysis experiment has also been carried out with the $Zn.Cr_2O_3$ catalyst. The operation conditions were 100° C., 25 bar and a feed consisting of a PC:water mixture of 3:1 molar ratio introduced at the higher space velocity of WHSV=5 g/g/h and a $N_2$ flow of 2.1 µg/h. Under these conditions, the $Zn.Cr_2O_3$ catalyst allowed an MPG yield of 15.4 mole % without formation of side products in detectable amounts. Under enhanced aging conditions at 160° C., the leaching rate of zinc species amounted to ~0.05 mg Zn/kg liquid product. For comparison, a blank experiment run with a SiC bed allowed an MPG yield of 0.2 mole % only under these conditions. Similar results are obtainable with the other zinc supported catalysts of the invention.

What is claimed:

1. A method for the catalytic conversion of an organic carbonate to a corresponding alcohol comprising:
    contacting the organic carbonate with an alcohol and/or water in the presence of a zinc supported catalyst.

2. The method of claim 1, wherein the zinc supported catalyst comprises a support material which is selected from the group consisting of $SiO_2$, $Al_2O_3$, MgO, $TiO_2$, $ZrO_2$, $Cr_2O_3$, C and mixtures thereof.

3. The method of claim 2, wherein the zinc supported catalyst is formed by a method comprising impregnating the support material with a zinc salt or a metallic or organometallic species.

4. The method of claim 2, wherein the zinc supported catalyst is formed by a method comprising co-kneading or co-precipitating a zinc salt with the salt of another metal.

5. The method of claim 1, wherein the zinc supported catalyst is calcinated at a temperature in the range of from 200° C. to 800° C.

6. The method of claim 1, wherein the alcohol is selected from the group consisting of an aromatic ($C_5$–$C_9$) alcohol and an aliphatic $C_1$–$C_{30}$ alcohol.

7. The method of claim 6, wherein the aromatic alcohol comprises phenol.

8. The method of claim 6, wherein the aliphatic alcohol is a saturated or unsaturated $C_1$–$C_{10}$-alkylalcohol.

9. The method of claim 1, wherein the organic carbonate is selected from the group consisting of dialkyl carbonate, diaryl carbonate, alkylaryl carbonate, and arylalkyl carbonate, wherein the alkyl and/or aryl groups may be linked together.

10. The method of claim 1 wherein the molar ratio between water and alcohol is in the range of from 1:1 to 1:100.

* * * * *